United States Patent [19]

Regnier et al.

[11] Patent Number: 4,514,399
[45] Date of Patent: Apr. 30, 1985

[54] N-N'SUBSTITUTED POLYMETHYLENE DIAMINES

[75] Inventors: Gilbert Regnier, Chatenay Malabry; Alain Dhainaut, Chatou; Michel Laubie, Vaucresson; Jacques Duhault, Croissy-Sur-Seine, all of France

[73] Assignee: Adir, Neuilly-sur-Seine, France

[21] Appl. No.: 486,013

[22] Filed: Apr. 18, 1983

[30] Foreign Application Priority Data

Apr. 21, 1982 [FR] France ............... 82 06813

[51] Int. Cl.³ .............. C07D 251/70; A61K 31/53
[52] U.S. Cl. ........................... 514/241; 544/196; 544/197; 544/198
[58] Field of Search ............ 544/196, 197, 198; 542/423, 425; 424/249

[56] References Cited

U.S. PATENT DOCUMENTS 3,310,557 3/1967 Kleemann .................. 544/197
4,261,892 4/1981 Tomcufcik et al. ............ 544/197

OTHER PUBLICATIONS

Hamburger, "Ditionaire de Medecine", p. 407, Flammarion Medecine, Sciences, (1982).

Primary Examiner—John M. Ford
Attorney, Agent, or Firm—Gordon W. Hueschen

[57] ABSTRACT

N,N'-substituted polymethylene diamines of the formula:

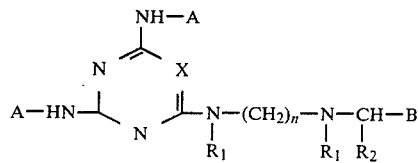

in which:

A is a hydrocarbon radical from $C_3$ to $C_5$ in a straight or branched chain optionally containing one and two double bonds and possibly substituted by one or more hydroxy radicals;

X is CH or nitrogen;

n is an integer from 2 to 6;

$R_1$ is hydrogen, or alkyl from $C_1$ to $C_5$;

$R_2$ is hydrogen, alkyl from $C_1$ to $C_5$, cycloalkyl from $C_5$ to $C_7$, or phenyl optionally substituted by one or more fluorine or chlorine, and B is:

phenyl, naphthyl, benzofuranyl, benzothionyl, benzodioxolyl, benzodioxanyl, benzodioxinyl, Δ3-chromenyl, thiochromenyl or chromanyl, each of them optionally substituted by fluorine, chlorine, alkyl or alkoxy from $C_1$ to $C_5$, or methylene-dioxy, or a radical of the formula:

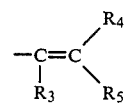

in which $R_3$, $R_4$ and $R_5$ which may be the same or different, each represent hydrogen or phenyl optionally substituted by fluorine or chlorine.

These compounds and physiologically tolerable acid addition salts thereof may be used as medicines especially in the treatment of all kinds of tissular hypoxia.

6 Claims, No Drawings

N-N'SUBSTITUTED POLYMETHYLENE DIAMINES

The present invention provides N,N'-substituted polymethylene diamines of the formula:

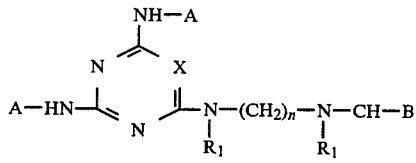

in which:

A is selected from the group consisting of: saturated hydrocarbon radicals containing from 3 to 5 carbon atoms inclusive, in straight and branched chain, the corresponding unsaturated hydrocarbon radicals containing one and two double bonds, and the corresponding mono- and di-hydroxy (saturated and unsaturated) hydrocarbon radicals;

X is selected from the group consisting of —CH— and a nitrogen atom;

n is selected from the group consisting of the integers from 2 to 6 inclusive;

$R_1$ is selected from the group consisting of: a hydrogen atom, and alkyl radicals having from 1 to 5 carbon atoms inclusive;

$R_2$ is selected from the group consisting of: a hydrogen atom, alkyl radicals having from 1 to 5 carbon atoms inclusive, cycloalkyl radicals having from 5 to 7 carbon atoms inclusive, an unsubstituted phenyl radical and phenyl radicals mono- and poly-substituted by a substituent selected from the group consisting of fluorine and chlorine atoms; and B is selected from the group consisting of:

phenyl, naphthyl, benzofuranyl, benzothienyl, benzodioxolyl, benzodioxanyl, benzodioxinyl, Δ3-chromenyl, thiochromenyl and chromanyl radicals, and each of these radicals mono- and poly-substituted by a substituent selected from the group consisting of fluorine and chlorine atoms, alkyl and alkoxy radicals each having from 1 to 5 carbon atoms inclusive, and methylene dioxy; and a radical of the formula:

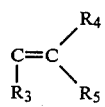

in which: $R_3$, $R_4$ and $R_5$, which may be the same or different, are each selected from the group consisting of a hydrogen atom, an unsubstituted phenyl radical and phenyl radicals mono- and polysubstituted by a substituent selected from the group consisting of: chlorine and fluorine atoms.

The present invention further provides a process for preparing the compounds of the formula I, in which:

a diamine of the formula II:

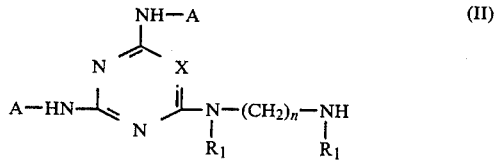

in which A, X, n and $R_1$ have the previously stated definitions, is condensed with a halo compound of the formula III:

in which $R_2$ and B have the previously defined significances, and Hal represents a halogen atom such for example as an atom of chlorine or bromine.

The condensation is preferably carried out in a solvent chosen from the high boiling point benzene hydrocarbons such as toluene or xylene, the aliphatic amides such as dimethylformamide or dimethylacetamide possibly mixed with high boiling point benzene hydrocarbons or with methylcyanide. It is advantageous to operate at a temperature between 120° and 140° C. in the presence of an acceptor of the hydracid formed in the course of the reaction. This acceptor may be chosen from the alkaline carbonates such as potassium carbonate, triethylamine, or an excess of the diamine of formula II used for the condensation.

The present invention also provides a process for preparing the compounds of the formula I, characterised in that a halo compound of the formula IV:

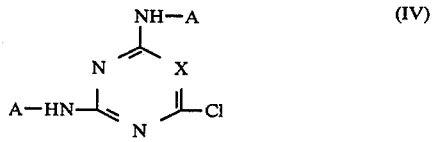

in which A and X have the previously defined significances, is condensed with a diamine of the formula V:

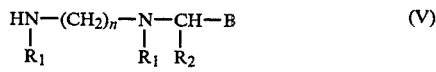

in which $R_1$, $R_2$, n and B have the previously stated significances.

The condensation is carried out in a particularly satisfactory way in a solvent chosen from the $C_4$ or $C_5$ alcohols such as butanol or pentanol, and the aliphatic amides such as dimethylformamide or dimethylacetamide. It is recommended to operate at a temperature between 120° and 150° C. in the presence of an acceptor of the hydracid formed in the course of the reaction.

This acceptor may be chosen from the alkaline carbonates such as potassium carbonate, triethylamine, or an excess of the amine of the formula V previously defined.

The present invention also provides a process for preparing the compounds of the formula I':

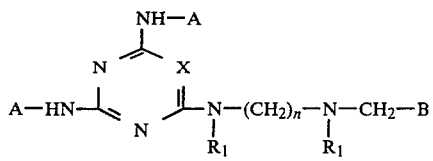

in which A, X, n, $R_1$ and B are as previously defined, characterised in that the corresponding amide of the formula VI:

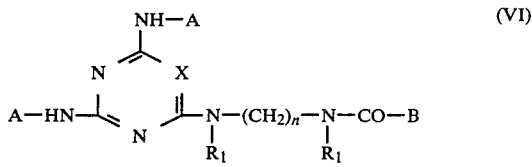

in which A, X, n, $R_1$ and B are as previously defined, is reduced.

As reducing agent, there can be used for example the double hydride of lithium and aluminium: $LiAlH_4$ or boron hydride: $B_2H_6$.

A particularly suitable method of working consists in carrying out the reduction in a solvent such as tetrahydrofuran at a temperature between 20° and 60° C.

These so obtained new compounds may be converted into salts of addition with acids, which salts therefore form part of the invention. As acids which may be used for the formation of these salts there may for example be cited in the mineral series hydrochloric, hydrobromic, sulfuric and phosphoric acids, and in the organic series, acetic, propionic, maleic, fumaric, tartaric, nitric, oxalic, benzoic, methane sulfonic and isethionic acids.

These new compounds may be purified by physical methods such as crystallisation and chromatography, or chemical methods such as the formation of salts of addition with acids and decomposition of these salts by alkaline agents.

The starting materials used in the previously described processes are either known products, or products prepared starting from known substances, according to processes described for the preparation of similar products as indicated in the following examples.

The compounds of the formula I and physiologically tolerable addition salts thereof possess interesting pharmacological ans therapeutic properties. In particular, they favour the capture of oxygen and thus enable them to be used as medicine, notably in the treatment of all kinds of tissular hypoxia.

In addition, these derivatives and their physiologically tolerable salts present a very weak toxicity.

The effect of the compounds of the invention on oxygen pressure (P $O_2$) has been studied in dogs anaesthetized with Nembutal. Samples of blood were taken periodically 2, 5, 15, 45, and 75 minutes after the administration of the compounds under test; they were used for the determination of the pH, of the P $O_2$, and of the P $CO_2$.

The P $O_2$ is measured on a radiometer apparatus BMS3. The reading of the P $O_2$ is done on this apparatus after it is previously standardised with known values, by means of a platinum electrode or a Clark electrode.

The products have been administered to dogs by intravenous route at a dose of 1 mg/kg and the determination of the percentage increase of the content of oxygen in the arterial blood shows that this percentage depending on the compound, can reach up to 37%, 45 minutes after the administration of the compound, and up to 43%, 75 minutes after the administration of the compound.

The products of the present invention were also shown to be active in the treatment of anemic hypoxia induced by chemical route with a subcutaneous injection of $NaNO_2$, according to Gibson G.E.'s method, Neurobiol. Aging 2, 165, (1981) and Biochem. Pharmacol. 28, 747, (1979), and in hypobaric hypoxia according to the technic of Legeai J.M. and als, Experientia 37, 292 (1981).

The present invention also provides the pharmaceutical compositions containing as active ingredient a compound of the formula I or one of its physiologically tolerable salts, mixed or associated with an appropriate pharmaceutical carrier.

The pharmaceutical compositions thus obtained are advantageously in unit dosage forms and may contain from 20 to 100 mg of active ingredient. These pharmaceutical compositions are advantageously presented in various dose forms such for example as tablets, sugar-coated tablets, capsules, suppositories, injectable or drinkable solutions. They may be administered by oral, rectal or parenteral route at doses of 20 to 100 mg once or twice a day.

The following examples illustrate the invention.

EXAMPLE 1

N-ethyl N-(4,6-bis allylamino s.triazin-2-yl) N'-ethyl N'-(bis p.fluorobenzhydryl) ethylenediamine

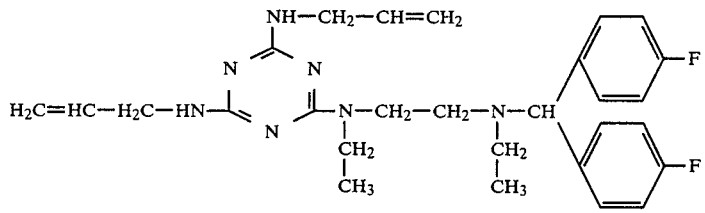

1st method

A solution of 6.1 g of N-(4,6-bis allylamino s.triazin-2-yl) N,N'-diethyl ethylene diamine and 5.7 g of bis p.fluorobenzhydryl bromide in 100 ml of toluene containing 5% of dimethylformamide, was heated for 8 hours at reflux, in the presence of 2 g of triethylamine. It was then cooled, taken up with 100 ml of water, decanted, and extracted twice with 50 ml of normal solution of monomethane sulphonic acid.

The acid solution was then washed with ether, then alkalized to pH 9 with $K_2CO_3$, and then extracted several times with chloroform. After evaporating the chloroform a crude oil was recovered which was crystallised from 160 ml of ethanol. Finally 6.8 g of N-ethyl N-(4,6-bis allylamino s.triazin-2-yl) N'-ethyl N'-(bis p.fluorobenzhydryl) ethylene diamine, was isolated in the form of crystals melting (capillary) at 105° to 107° C. The starting amine, of which the difumarate melts (Kofler) at 204° C. has been prepared by heating 2,4-bis allylamino-6-chloro-s.triazine in an excess of N,N'-diethyl ethylene diamine at 140° C.

2nd method

A solution of 4.25 g of 4,6-bis allylamino-2-chloro s.triazine and 6 g of N,N'-diethyl N-(bis p.fluorobenzhydryl) ethylene diamine in 50 ml of butanol, is heated for 5 hours at reflux in the presence of 100 mg of sodium iodide and 2.6 ml of triethylamine. The solvent is then driven off under reduced pressure, the residue is recrystallized from 160 ml of ethanol at 70%. 5.2 g of N-ethyl N-(4,6-bis allylamino s.triazin-2-yl) N'-ethyl N'-(bis p.fluorobenzhydryl) ethylene diamine, is obtained in the form of crystals melting (capillary) at 105° to 107° C. The starting amine (BP/27Pa=154°–156° C.) has been prepared by heating bis p.fluorobenzhydryl bromide in an excess of N,N'-diethyl ethylene diamine.

M.P. (Kofler) of the corresponding fumarate: 148° C. (ethanol).

(10) N-ethyl N-(4,6-bis allylamino s.triazin-2-yl) N'-ethyl N'-(bis p.fluorobenzhydryl) trimethylene diamine M.P. (Kofler) of the corresponding difumarate: 125° C. (anhydrous ethanol).

(11) N-ethyl N-(4,6-bis allylamino s.triazin-2-yl) N'-ethyl N'-cinnamyl ethylene diamine, M.P. (Kofler) of the corresponding dioxalate: 171°–173° C.

(12) N-ethyl N-(4,6-bis allylamino s.triazin-2-yl) N'-ethyl N'-(3,3-bis p.fluorophenyl allyl) ethylene diamine.

(13) N-ethyl N-(4,6-bis allylamino s.triazin-2-yl) N'-ethyl N'-(benzothien-2-yl methyl) trimethylene diamine, M.P. (Kofler) of the corresponding difumarate: 130° C. (anhydrous ethanol).

(14) N-ethyl N-(4,6-bis allylamino s.triazin-2-yl) N'-ethyl N'-cinnamyl trimethylene diamine, M.P. (capillary) of the corresponding difumarate: 114°–116° C. (anhydrous ethanol).

EXAMPLE 15

N-ethyl N-(4,6-bis allylamino s.triazin-2-yl) N'-ethyl N'-(benzothien-2-yl methyl) ethylene diamine

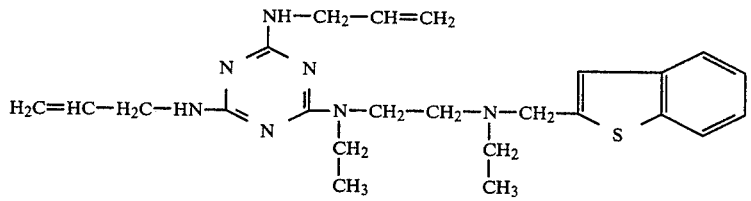

EXAMPLES 2 to 14

The following compounds have been prepared according to the methods described in example 1:

(2) N-(4,6-bis allylamino s.triazin-2-yl) N'-(bis p.fluorobenzhydryl) ethylene diamine, M.P. (capillary) of the corresponding difumarate: 185°–187° C. (ethanol).

(3) N-methyl N-(4,6-bis allylamino s.triazin-2-yl) N'-methyl N'-(bis p.fluorobenzhydryl) ethylene diamine, M.P. (capillary) of the corresponding difumarate: 139°–142° C. (ethanol).

(4) N-(4,6-bis allylamino s.triazin-2-yl) N'-(bis p.fluorobenzhydryl) trimethylene diamine, M.P. (capillary) of the corresponding difumarate: 177°–179° C. (ethanol).

(5) N-(4,6-bis allylamino s.triazin-2-yl) N'-(α-cyclopentyl p.fluorobenzyl) ethylene diamine, M.P. (Kofler) of the corresponding difumarate: 117° C. (ethanol).

(6) N-(4,6-bis allylamino s.triazin-2-yl) N-(α-cyclohexyl p.fluorobenzyl) ethylene diamine, M.P. (Kofler) of the corresponding difumarate: 204° C. (ethanol).

(7) N-ethyl N-(4,6-bis allylamino s.triazin-2-yl) N'-ethyl N'-(p.fluorobenzyl) ethylene diamine, M.P. (Kofler) of the corresponding trifumarate: 154° C. (anhydrous ethanol).

(8) N-ethyl N-(4,6-bis allylamino s.triazin-2-yl) N'-ethyl N'-(benzofuran-2-yl methyl) ethylene diamine, M.P. (Kofler) of the corresponding difumarate: 162° C. (ethanol).

(9) N-ethyl N-(4,6-bis allylamino s.triazin-2-yl) N'-ethyl N'-(benzothien-2-yl methyl) ethylene diamine, A solution of 9.3 g of N-ethyl N-(4,6-bis allylamino s.triazin-2-yl) N'-ethyl N'-(benzothien-2-yl carbonyl) ethylene diamine, M.P. (Kofler) of the corresponding fumarate 180° C., in 200 ml of tetrahydrofuran is heated for 18 hours at reflux in the presence of 2.28 g of Li Al H$_4$. At the end of this time it is cooled under nitrogen and the complex is hydrolised with successively 2.28 ml of water, 2.28 ml of a 4N solution of sodium hydroxide and 7 ml of water. The alumina formed is filtered off and the filtrate is evaporated to dryness. This is taken up by 200 ml of ether, washed with water, decanted, and the ether is dried. After evaporation of the solvent, the fumarate is prepared starting with the crude oil, in ethanol 7 g of fumarate crystals of N-ethyl N-(4,6-bis allylamino s.triazin-2-yl) N'-ethyl N'-(benzothien-2-yl methyl) ethylene diamine, melting (Kofler) at 148° C. is recovered. The starting amide has been prepared starting from benzothien-2-yl carboxylic acid chloride and the difumarate of N-(4,6-bis allylamino s.triazin-2-yl) N,N'-diethyl ethylene diamine, M.P. (Kofler): 240° C., in tetrahydrofuran in the presence of the triethylamine.

EXAMPLES 16 to 19

The following compounds have been prepared according to the method described in example 15:

(16) N-ethyl N-(4,6-bis allylamino s.triazin-2-yl) N'-ethyl N'-(p.fluorobenzyl) ethylene diamine, M.P. (Kofler) of the corresponding difumarate 204° C. (ethanol).

(17) N-ethyl N-(4,6-bis allylamino s.triazin-2-yl) N'-ethyl N'-(benzofuran-2-yl methyl) ethylene diamine, M.P. (Kofler) of the corresponding difumarate: 162° C. (ethanol).

(18) N-ethyl N-(4,6-bis allylamino s.triazin-2-yl) N'-ethyl N'-cinnamyl ethylene diamine, M.P. (Kofler) of the corresponding dioxalate: 171°–173° C.

(19) N-ethyl N-(4,6-bis allylamino s.triazin-2-yl) N'-ethyl N'-(3,3-bis p.fluorophenyl allyl) ethylene diamine.

We claim:

1. A compound selected from the group consisting of: N,N'-substituted polymethylene diamines of the formula I:

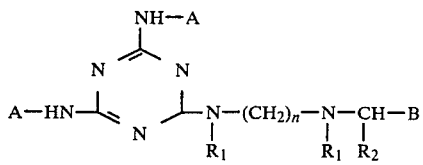

in which:

A is selected from the group consisting of: saturated hydrocarbon radicals containing 3 to 5 carbon atoms inclusive, in straight and branched chain, the corresponding unsaturated hydrocarbon radicals containing one and two double bonds, and the corresponding mono- and di-hydroxy (saturated and unsaturated) hydrocarbon radicals;

n is selected from the group consisting of the integers 2 to 6 inclusive;

$R_1$ is selected from the group consisting of: hydrogen and alkyl having 1 to 5 carbon atoms inclusive;

$R_2$ is selected from the group consisting of: hydrogen, alkyl having 1 to 5 carbon atoms inclusive, cycloalkyl having 5 to 7 carbon atoms inclusive, unsubstituted phenyl and phenyl mono- and poly-substituted by a substituent selected from the group consisting of fluorine and chlorine; and B is selected from the group consisting of: bis-fluorobenzhydryl, alpha-cyclohexyl-fluorobenzyl, alpha-cyclopentyl-fluorobenzyl, fluorobenzyl, benzofuran-2-yl methyl, and benzylthien-2-yl methyl,; and a radical of the formula:

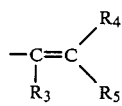

in which: $R_3$, $R_4$ and $R_5$, which may be the same or different, are each selected from the group consisting of hydrogen, unsubstituted phenyl and phenyl mono- and polysubstituted by a substituent selected from the group consisting of: chlorine and fluorine; and physiologically tolerable acid addition salts thereof.

2. A compound of claim 1 which is N-ethyl N-(4,6-bis allylamino s.triazin-2-yl) N'-ethyl N'-(bis p.fluorobenzhydryl) ethylene diamine.

3. A compound of claim 1 which is N-ethyl N-(4,6-bis allylamino s.triazin-2-yl) N'-ethyl N'-(bis p.fluorobenzhydryl) trimethylene diamine, and its difumarate.

4. A compound of claim 1 which is: N-ethyl N-(4,6-bis allylamino s.triazin-2-yl) N'-ethyl N'-(benzothien-2-yl methyl) ethylene diamine, and its fumarate.

5. A pharmaceutical composition, suitable for use in the treatment of hypoxia, containing as active ingredient a compound selected from the group consisting of: N,N'-substituted polymethylene diamines of the formula I:

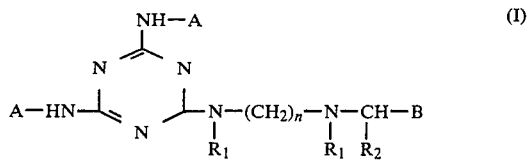

in which:

A is selected from the group consisting of: saturated hydrocarbon radicals containing 3 to 5 carbon atoms inclusive, in straight and branched chain, the corresponding unsaturated hydrocarbon radicals containing one and two double bonds, and the corresponding mono- di-hydroxy (saturated and unsaturated) hydrocarbon radicals;

n is selected from the group consisting of the integers 2 to 6 inclusive;

$R_1$ is selected from the group consisting of: hydrogen and alkyl having 1 to 5 carbon atoms inclusive;

$R_2$ is selected from the group consisting of: hydrogen, alkyl having 1 to 5 carbon atoms inclusive, cycloalkyl having 5 to 7 carbon atoms inclusive, unsubstituted phenyl and phenyl mono- and poly-substituted by a substituent selected from the group consisting of fluorine and chlorine; and B is selected from the group consisting of: phenyl, naphthyl, benzofuranyl, benzothienyl, benzodioxolyl, benzodioxanyl, benzodioxinyl, 3-chromenyl, thiochromenyl and chromanyl and each of these radicals mono- and poly-substituted by a substituent selected from the group consisting of fluorine and chlorine, alkyl and alkoxy each having 1 to 5 carbon atoms inclusive, and methylene dioxy; and a radical of the formula:

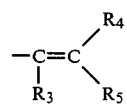

in which: $R_3$, $R_4$ and $R_5$, which may be the same or different, are each selected from the group consisting of hydrogen, unsubstituted phenyl and phenyl mono- and poly-substituted by a substituent selected from the group consisting of chlorine and fluorine; and physiologically tolerable acid addition salts thereof, in an amount effective for such purpose, together with a suitable pharmaceutical carrier.

6. A method for treating a living animal body afflicted with a tissular hypoxia, comprising the step of administering to the said living animal an amount of a compound selected from the group consisting of N,N'-substituted polymethylene diamines of the formula I:

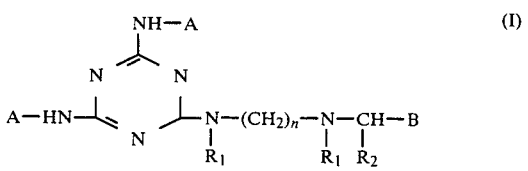

in which:

A is selected from the group consisting of: saturated hydrocarbon radicals containing 3 to 5 carbon atoms inclusive, in straight and branched chain, the corresponding unsaturated hydrocarbon radicals containing one and two double bonds, and the corresponding mono- and di-hydroxy (saturated and unsaturated) hydrocarbon radicals;

n is selected from the group consisting of the integers 2 to 6 inclusive;

$R_1$ is selected from the group consisting of: hydrogen and alkyl having 1 to 5 carbon atoms inclusive;

$R_2$ is selected from the group consisting of: hydrogen, alkyl having 1 to 5 carbon atoms inclusive, cycloalkyl having 5 to 7 carbon atoms inclusive, unsubstituted phenyl and phenyl mono- and poly-substituted by a substitutent selected from the group consisting of fluorine and chlorine; and B is selected from the group consisting of: phenyl, naphthyl, benzofuranyl, benzothienyl, benzodioxolyl, benzodioxanyl, benzodioxinyl, 3-chromenyl, thiochromenyl and chromanyl and each of these radicals mono- and poly-substituted by a substituent selected from the group consisting of fluorine and chlorine, alkyl and alkoxy each having 1 to 5 carbon atoms inclusive, and methylene dioxy; and a radical of the formula:

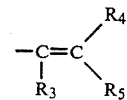

in which: $R_3$, $R_4$ and $R_5$, which may be the same or different, are each selected from the group consisting of hydrogen, unsubstituted phenyl and phenyl mono- and poly-substituted by a substituent selected from the group consisting of chlorine and fluorine; and physiologically tolerable acid addition salts thereof, which is effective for the alleviation of the said condition.

* * * * *

UNITED STATES PATENT AND TRADEMARK OFFICE
CERTIFICATE OF CORRECTION

PATENT NO. : 4,514,399

DATED : April 30, 1985

INVENTOR(S) : Gilbert Regnier et al.

It is certified that error appears in the above-identified patent and that said Letters Patent is hereby corrected as shown below:

Title page, item [56], References Cited, OTHER PUBLICATIONS, line 1;
  "Ditionaire" should read -- Ditionnaire -- Notice of References Cited,
  attachment to Paper No. 8, dated July 13, 1984
Title page, item [57], ABSTRACT, 13th line after the first formula;
  "benzothionyl" should read -- benzothienyl --
Title page, item [57], ABSTRACT, 2nd line after the second formula; after
  "hydrogen" insert a comma -- , --
Col. 1, formula I; add -- $R_2$ -- under "CH" at the end of the formula as shown:

Col. 3, line 59; "ans" should read -- and --
Col. 7, formula I and Col. 8, formula I (both occurrences), change

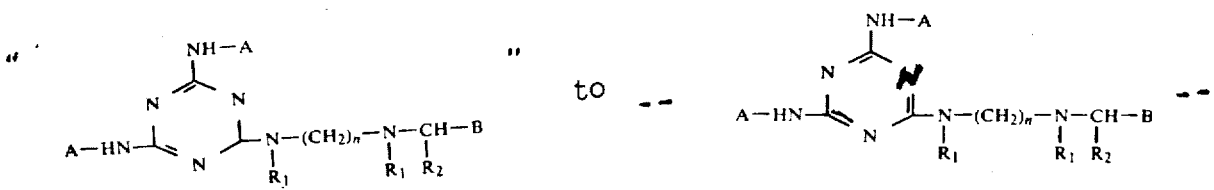

$$\text{Signed and Sealed this}$$

Fifth Day of November 1985

[SEAL]

Attest:

DONALD J. QUIGG

Attesting Officer

Commissioner of Patents and Trademarks